US011344607B2

(12) United States Patent
Garvin et al.

(10) Patent No.: US 11,344,607 B2
(45) Date of Patent: May 31, 2022

(54) TREATMENT OF DISEASE WITH RELAXIN (71) Applicant: BV Biomed Ltd, Glasgow (GB)

(72) Inventors: Roy Garvin, Glasgow (GB); Alasdair Burns, Glasgow (GB)

(73) Assignee: BV BIOMED LTD, Glasgow (GB)

(*) Notice: Subject to any disclaimer, the term of this patent is extended or adjusted under 35 U.S.C. 154(b) by 0 days.

(21) Appl. No.: 15/759,060

(22) PCT Filed: Sep. 9, 2016

(86) PCT No.: PCT/GB2016/052792
§ 371 (c)(1),
(2) Date: Mar. 9, 2018

(87) PCT Pub. No.: WO2017/042577
PCT Pub. Date: Mar. 16, 2017

(65) Prior Publication Data
US 2019/0000927 A1    Jan. 3, 2019

(30) Foreign Application Priority Data
Sep. 10, 2015  (GB) ................................. 1516068

(51) Int. Cl.
*A61K 38/22*   (2006.01)
*A61K 31/565*  (2006.01)
*A61P 25/00*   (2006.01)
*A61P 25/02*   (2006.01)
*A61K 45/06*   (2006.01)
*A61P 29/00*   (2006.01)

(52) U.S. Cl.
CPC ........ *A61K 38/2221* (2013.01); *A61K 31/565* (2013.01); *A61K 45/06* (2013.01); *A61P 25/00* (2018.01); *A61P 25/02* (2018.01); *A61P 29/00* (2018.01)

(58) Field of Classification Search
None
See application file for complete search history.

(56) References Cited

U.S. PATENT DOCUMENTS

2013/0012441 A1* 1/2013 Stewart .................. C07K 16/26
                                                      514/12.7
2014/0066377 A1* 3/2014 Parry .................. A61K 38/2221
                                                      514/12.7

FOREIGN PATENT DOCUMENTS

| IT | WO 95/03822 | * | 2/1995 | ............. A61K 38/22 |
| WO | WO 00/48618 | * | 2/2000 | ............. A61K 38/00 |
| WO | WO 00/13652 A2 | | 3/2000 | |
| WO | WO 00/48618 | | 8/2000 | |
| WO | WO 03/030930 A1 | | 4/2003 | |
| WO | WO 2012/175744 A1 | | 12/2012 | |
| WO | WO 2013/090318 | | 6/2013 | |
| WO | WO 2013/172969 | * | 11/2013 | ............. A01N 43/04 |
| WO | WO 2014/022294 A1 | | 2/2014 | |

OTHER PUBLICATIONS

Bhattacharya et al., PLoS ONE 12(3): e0171355. https://doi.org/10.1371/journal.pone.0171355; 22 pages total (Year: 2017).*
Tokuriki and Tawflik, Current Opinion in Structural Biology 2009, 19: 596-604 (Year: 2009).*
Phillips, A., J Pharm Pharmacology, 2001; 53: 1169-1174 (Year: 2001).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
Ghirnikar et al. (Neurochemical Research, 1998; 23: 329-340 (Year: 1998).*
Praveen et al., Molecular and Cellular Endocrinology, 2019; 487: 34-39 (Year: 2019).*
The website at www.healthline.com/health/head-injury#outlook; downloaded Sep. 16, 2019; 13 pages total (Year: 2019).*
Fuschiotti, Immunology Letters, 2018; 195: 55-60 (Year: 2018).*
Aida-Yasuoka et al., Arthritis Research & Therapy 2013, 15: R10 (Year: 2013).*
Burda and Sofroniew, Neuron, Jan. 22, 2014; 81: 229-248 (Year: 2014).*
Nayeri et al., Hypertension, Jun. 2014; 63: 1285-1292 (Year: 2014).*
O. David Sherwood, Endocrine Reviews 25(2):205-234 (Year: 2004).*
Shi et al., Exp Neurol. Author manuscript; available in PMC Sep. 24, 2016 (Year: 2016).*
O'Connor et al., Brain Research 1062 (2005) 171-174 (Year: 2005).*
James J. Donkin and Robert Vink, Curr Opin Neurol 23:293-299 (Year: 2010).*
Sarah Claire Hellewell and Maria Cristina Morganti-Kossmann, Mediators of Inflammation, 2012, Article ID 356494, 18 pages; doi: 10.1155/2012/356494 (Year: 2012).*
Milia et al., Italian Journal of Anatomy and Embryology, 2013, vol. 118, n.1 (Suppl .): 92-97 (Year: 2013).*
Lawrence Brass, Stroke. 2004;35[suppl 1]:2644-2647 (Year: 2004).*
Day et al., Journal of Neurotrauma 2013; 30: 1531-1541 (Year: 2013).*
Schroeter and Jander; doi: 10.1385/NMM:7:3:183 (Year: 2005).*
The website https://www.biausa.org/brain-injury/about-brain-injury/nbiic/what-is-the-difference-between-an-acquired-brain-injury-and-a-traumatic-brain-injury, downloaded Aug. 23, 2021; 4 pages total (Year: 2021).*
Anderton, S.M., "Treg and T-effector Cells in Autoimmune CNS Inflammation: A Delicate Balance, Easily Disturbed," *Eur. J. Immunol.*, vol. 40, No. 12, pp. 3321-3324, (2010); DOI: 10.1002/eji.201041100.
Barrett-Connor, E., et al., "Hormone Replacement Therapy (HRT)—Risks and Benefits," *Int. J. Epidemiol.*, vol. 30, No. 3, pp. 423-426, (2001); DOI: 10.1093/ije/30.3.423.

(Continued)

*Primary Examiner* — Christina M Borgeest
(74) *Attorney, Agent, or Firm* — Hoxie & Associates LLC (57) ABSTRACT

The present invention relates to relaxin or a homologue or variant thereof for use in a method of treating an inflammatory condition, for example an autoimmune inflammatory condition. The invention also relates to the treatment of an inflammatory condition, for example an autoimmune inflammatory condition comprising administering to a subject in need thereof a relaxin, or a homologue or variant thereof. Such conditions may be CNS conditions or be organ specific.

3 Claims, 6 Drawing Sheets

(56) References Cited

OTHER PUBLICATIONS

Bellone, M., "Autoimmune Disease: Pathogenesis," *In: eLS. John Wiley & Sons Ltd, Chichester*, http://www.els.net/WieyCDA/ElsArticle/refId-a0001276.html, (2015); DOI: 10.1002/9780470015902.a0001276.pub4.

Cai, Y., et al., "New Insights of T Cells in the Pathogenesis of Psoriasis," *Cellular & Molecular Immunology*, vol. 9, pp. 302-309, (2012); DOI: 10.1038/cmi.2012.15.

Constantinescu, C.S., et al., "Experimental Autoimmune Encephalomyelitis (EAE) as a Model for Multiple Sclerosis (MS)", *British Journal of Pharmacology*, vol. 164, No. 4, pp. 1079-1106, (2011); DOI: 10.1111/j.1476-5381.2011.01302.x.

Costello, K., et al., "Recognizing Nonadherence in Patients with Multiple Sclerosis and Maintaining Treatment Adherence in the Long Term," *Medscape J. Med.*, vol. 10, No. 9, pp. 1-14, (2008).

Garg, R.K., "Acute Disseminated Encephalomyelitis," *Postgrad. Med. J.*, vol. 79, No. 927, pp. 11-17, (2003).

He, F., et al., "The Role of Regulatory T Cells in Neurodegenerative Diseases," *WIREs Syst. Biol. Med.*, vol. 5, No. 2, pp. 153-180, (2013); DOI: 10.1002/wsbm.1187.

Leavy, O., "T Cells: Two Faces of EAE," *Nature Reviews Immunology*, vol. 8, pp. 576, (2008).

Santora, K., et al., "Effects of Relaxin in a Model of Rat Adjuvant-Induced Arthritis," *Annals of the New York Academy of Sciences*, vol. 1041, pp. 481-485, XP009101310, (2005).

Schwartz, M., et al., "Boosting T-Cell Immunity as a Therapeutic Approach for Neurodegenerative Conditions: The Role of Innate Immunity," *Neuroscience*, vol. 158, No. 3, pp. 1133-1142, (2009); DOI: 10.1016/j.neuroscience.2008.12.013.

Shao, H., et al., "Myelin/Oligodendrocyte Glycoprotein-Specific T-Cells Induce Severe Optic Neuritis in the C57Bl/6 Mouse," *Invest. Ophthalmal. Vis. Sci.*, vol. 45, No. 11, pp. 4060-4065, (2004); DOI: 10.1167/iovs.04-0554.

Sicotte, N.L., et al., "Treatment of Multiple Sclerosis with the Pregnancy Hormone Estriol.," *Ann. Neurol.*, vol. 52, No. 4, pp. 421-428, (2002); DOI: 10.1002/ana.10301.

Smith, M.C., et al., "Influence of Recombinant Human Relaxin on Renal Hemodynamics in Healthy Volunteers," *J Am. Soc. Nephrol.*, vol. 17, pp. 3192-3197, (2006); DOI: 10.1681/ASN.2005090950.

Weiner, H.L., "Multiple Sclerosis is an Inflammatory T-cell-mediated Autoimmune Disease," *Arch. Neurol.*, vol. 61, No. 10, pp. 1613-1615, (2004).

Garvin, R., "Treatment with Relaxin Reduces Severity, Decreases Chemokine Receptors and Pro-Inflammatory cytokines in Experimental Autoimmune Encephalomyelitis in C57BL/6 mice," Ectrims 2015, Barcelona, Spain, Conference Poster, 2015, 2 pages.

International Search Report of International Application No. PCT/GB2016/052792, prepared by the International Searching Authority, dated Dec. 19, 2016, 4 pages.

Search Report of GB 1516068.2, prepared by the Intellectual Property Office of The United Kingdom, date prepared: May 25, 2016, 5 pages.

Santora, K., et al., "Antiarthritic Effects of Relaxin, in Combination with Estrogen, in Rat Adjuvant-Induced Arthritis," *Journal of Pharmacology and Experimental Therapeutics*, 2007, vol. 322(2):887-893.

Zeng, L., et al., "The Injury-Induced Myokine Insulin-like 6 is Protective in Experimental Autoimmune Myositis," *Skeletal Muscle*, 2014, vol. 4(16):1-14.

https://www.slideshare.net/BartsMSBlog/programme-ectrims2015 Linkedin Slideshare website "2015 Programme for the European committee for treatment and research in multiple sclerosis (ectrims) conference," Published by BARTSMS blog online on Jul. 19, 2015, 108 pages.

\* cited by examiner

Inflammation and Wallerian degeneration

Loss of Neurofilaments

GFAP ary inflammatory condition. The invention also relates to the treatment of an

TREATMENT OF DISEASE WITH RELAXIN

CROSS-REFERENCE TO RELATED APPLICATIONS

This application is a U.S. National Stage application of International Application No. PCT/GB2016/052792 filed on Sep. 9, 2016, which claims the benefit of and priority to British Provisional Patent Application No. 1516068.2, filed Sep. 10, 2015, the entirety of which is incorporated by reference herein.

FIELD OF THE INVENTION

The present invention relates to relaxin or a homologue or variant thereof for use in a method of treating an inflammatory condition, for example an autoimmune inflammatory condition. The invention also relates to the treatment of an inflammatory condition, for example an autoimmune inflammatory condition comprising administering to a subject in need thereof a relaxin, or a homologue or variant thereof. Such conditions may be CNS conditions or be organ specific.

BACKGROUND TO THE INVENTION

Experimental autoimmune encephalomyelitis, sometimes experimental allergic encephalomyelitis (EAE) is an animal model of brain inflammation. It is an inflammatory demyelinating disease of the central nervous system (CNS). It is mostly used with rodents and is widely studied as an animal model of the human CNS demyelinating diseases, including multiple sclerosis (MS) and acute disseminated encephalomyelitis (ADEM). EAE is also the prototype for T-cell-mediated autoimmune disease in general and may find relevance in other inflammatory conditions of the CNS.

EAE can be induced in a number of species, including mice, rats, guinea pigs, rabbits and primates. The most commonly used antigens in rodents are spinal cord homogenate (SCH), purified myelin, myelin protein such as MBP, PLP and MOG, or peptides of these proteins, all resulting in distinct models with different disease characteristics regarding both immunology and pathology. It may also be induced by the passive transfer of T cells specifically reactive to these myelin antigens. Depending on the antigen used and the genetic make-up of the animal, rodents can display a monophasic bout of EAE, a relapsing-remitting form, or chronic EAE.

EAE is a general model of inflammatory immuno diseases (see Weiner H L, 2004; Shao H, et al., 2004; Garg R K, 2003; Bellone, Matteo, 2010; and Cai Y, 2012). EAE is also considered as a model of inflammatory, autoimmune and neurodegenerative diseases through T cell regulation (see He F, 2013; Olive Leavy, 2008; Anderton S M, 2010; and M. Schwartz, 2008). EAE is a model of organ specific inflammatory autoimmune diseases (see Constantinescu C S, et al 2011).

WO2012/175744 describes the use of relaxin proteins and homologues for the diagnosis, prevention or treatment of MS, but there is no suggestion of preventing or treating other diseases.

WO0013652 describes the use of Relaxin to treat symptoms associated with aging and/or neurodegenerative dysfunctions. Many conditions including Alzheimer's disease and Parkinson's disease are mentioned in terms of alleviating symptoms, without describing any real treatment of neurodegenerative diseases.

It is amongst the objects of the present invention to provide novel therapies for treating inflammatory conditions, other than MS.

SUMMARY OF THE INVENTION

The present invention is based on studies by the present inventors into any effect relaxin has on an EAE mouse model.

In a first aspect there is provided a relaxin (RLX), a homologue or variant thereof, for use in a method of treating an inflammatory, autoimmune or neurodegenerative condition, other than MS, Alzheimer's disease and Parkinson's disease.

In a further aspect there is provided a method of treating an inflammatory, autoimmune or neurodegenerative condition, other than MS, Alzheimer's disease and Parkinson's disease, the method comprising administering a relaxin (RLX), a homologue or variant thereof to a subject in need thereof.

In a further aspect there is provided use of a relaxin (RLX), a homologue or variant thereof, for the manufacture of a medicament for use in a method of treating an inflammatory, autoimmune or neurodegenerative condition, other than MS, Alzheimer's disease and Parkinson's disease.

Typically the conditions to be treated may be associated with an aberrant T-cell response and the invention may be seen as being directed to T cell regulation. The inflammatory condition may be an inflammatory condition of the CNS and may include diseases or conditions which are also considered as being auto-immune diseases/conditions. These may include Diffuse cerebral sclerosis of Schilder; Acute disseminated encephalomyelitis; Acute hemorrhagic leukoencephalitis; Transverse myelitis; and Neuromyelitis optica. Other inflammatory conditions which may be treated include concussion and traumatic brain injury (TBI).

Through the studies carried out by the inventors, the inventors have observed that Relaxin decreases myelination and increases remyelination in the EAE model. In addition Relaxin treated mice display a complete lack of gliosis in contrast to untreated mice which show extensive gliosis. Thus, in accordance with an embodiment of the present invention diseases to be treated may include diseases which are associated and/or display gliosis.

Gliosis occurs as a result of many acute conditions such as trauma, ischemia, stroke is present in a wide variety of CNS pathologies. Gliosis involves hypertrophy or proliferation of glial cells, but the extent and nature of the gliosis response vary widely based on the triggering insult. Gliosis in any form entails an alteration in cellular activity that has the potential to create widespread effects on neurons as well as other non-neural cells, causing either a loss of normal functions or a gain of detrimental ones. Gliosis may be seen not only as a characteristic of many neuropathologies but as a potential contributor to, or even cause of, many CNS disease mechanisms. Diseases with gliosis include; CNS Trauma (Traumatic Brain Injury, Traumatic Spinal Cord Injury, Shaken Baby Syndrome, Concussion and Ionizing Radiation), Korsakoff's Syndrome, Multiple system Atrophy, Prion Disease, AIDS Dementia Complex, Vasculitis, Amyotrophic Lateral Sclerosis, and Huntington's disease, Autoimmune Inflammatory Disorders, Retinal Gliosis, Amyotrophic Lateral Sclerosis, encephalopathies, Leukodystrophies, Encephalitis and neuropathies.

Encephalopathy refers to degenerative brain injury which can be permanent or and reversible. It can be due to direct injury to the brain or illness remote from the brain. It refers to a wide variety of brain disorders with very different etiologies, prognoses and implications. For example, prion diseases, all of which cause transmissible spongiform encephalopathies, are invariably fatal, but other encephalopathies are reversible and can have a number of causes including nutritional deficiencies and toxins. Encephalopathies include; Acute Disseminated Encephalomyelitis, Hypoxic Ischemic Encephalopathy, (Permanent or transitory), Static Encephalopathy, Uremic Encephalopathy, Hashimoto's Encephalopathy, Hypertensive Encephalopathy, Chronic Traumatic Encephalopathy, Lyme Encephalopathy, Toxic Encephalopathy, Toxic-Metabolic Encephalopathy, Transmissible Spongiform Encephalopathy (Prion Disease), Neonatal Encephalopathy, Salmonella and Encephalomyopathy.

Leukodystrophies are rare diseases that affect the cells of the brain. Specifically, the diseases affect the myelin sheath, the material that surrounds and protects nerve cells. Damage to this sheath slows down or blocks messages between the brain and the rest of the body.

Most of the leukodystrophies are genetic. They usually appear during infancy or childhood. They can be hard to detect early because children seem healthy at first. However, symptoms gradually get worse over time and there are no cures for any of the leukodystrophies which include; Adrenomyeloneuropathy, Alexander Disease, Cerebrotendineous Xanthomatosis, Hereditary CNS Demyelinating Disease, Krabbe Disease, Metachromatic Leukodystrophy, Pelizaeus-Merzbacher Disease, Canavan Disease, Leukoencephalopathy with vanishing white matter, Adrenoleukodystrophy, Refsum Disease, Binswanger's disease, Zellweger Syndrome and Xenobefantosis.

Encephalomylitis is a group of disorders which start with inflammation of the CNS and can lead to neurodegeneration and gliosis. Encephalomylitic disorders with neurodegeneration and/or gliosis include; Acute Disseminated Encephalomyelitis or Postinfectious Encephalomyelitis, AIDS Related Encephalomyelitis, Anti-MOG Associated Encephalomyelitis, an underlying condition for neuromyelitis optica and in general all MOG autoantibody-associated demyelinating diseases.

Neuropathy describes a group of disorders which exhibit damage to the CNS or peripherial nervous system. These include; Diabetic Neuropathy, Extrapontine Myelinolysis, Viral mediated autoimmune disorders such as Fisher Syndrome and Guillain-Barre Syndrome, Optic Neuropathies, Systemic Lupus Erythematosus, Dimentias, AIDS Associated neuropathies, Attention Deficit Hyperactive Disorders, Ataxia Neuropathies and Chronic Inflammatory Demyelination Polyneuropathy.

The conditions to be treated may also relate to organ specific inflammatory autoimmune diseases, including Celiac disease, Sarcoidosis, Systemic lupus erythematosus, Sjogren's syndrome, Churg-Strauss Syndrome, Hashimoto's thyroiditis, Graves' disease, Idiopathic thrombocytopenic purpura, Addison's Disease, Polymyositis, Dermatomyositis, Myasthenia gravis, Psoriasis, and Chronic graft-versus-host disease.

Relaxin in terms of the present invention is understood to relate to relaxin 1 (RLX1) and/or relaxin 2 (RLX2). RLX1 and RXL2 are pleiotropic proteins which influence multiple pathways. RLX1 and RLX2 bind the relaxin family protein receptor 1 (RXFP 1), the glucocorticoid receptor (GR), the endothelin type-B receptor ($ET_B$) and the estrogen receptor β (ER1β). Binding of RLX1 and RLX2 to their receptor array results in the modulation of the $ET_R$, ER, GCR and RXFP1 receptor pathways. Through $ET_B$ RLX1 increases NF-dB and decreases endothelin-1 levels which leads to vasodilation.

Relaxin has been well defined in its natural human form, animal form, and in its synthetic form. In particular, relaxin has been extensively described in Cronin, et al., U.S. Pat. No. 5,166,191 and Burnier, et al., U.S. Pat. No. 4,835,251, both of which are hereby incorporated by reference. As used herein, "relaxin" will generally refer to the terms "relaxin", "human relaxin", "native relaxin", "relaxin homologue", and "synthetic relaxin". "Relaxin" is also understood to refer to relaxin as isolated from pigs, rats, horses and relaxin produced by recombinant techniques. In addition, "relaxin" will also refer to pro relaxin, preprorelaxin, relaxin homologues, derivatives, peptides with relaxin activity, as well as other relaxin variants obtained by addition, substitution, or deletions of one or more relaxin components.

The RLXs which are particularly useful in the present invention include RLX1 and RLX2 as well as variants and homologues of those proteins. Variants or homologues in the context of the present invention is intended to encompass proteins which are functionally equivalent to RLX1 and RLX2, but which have sequences which vary from the native ones. Such variants or homologues will also include functional fragments of the complete protein. Particularly preferred homologues include Prorelaxins and Preprorelaxins. As used herein "prorelaxin" refers to the prohormone form of relaxin which contains an additional peptide chain as compared to the heterodimer relaxin protein. "Preprorelaxin" refers to a precursor of prorelaxin which contains a secretory signal.

In the context of variants, in some embodiments, the relaxin polypeptide comprises one or more post-translational modifications. In some embodiments, the relaxin polypeptide may be linked to a linker, polymer, or biologically active molecule. In some embodiments, the relaxin polypeptide is linked to a bifunctional polymer, bifunctional linker, or at least one additional relaxin polypeptide. In some embodiments of the present invention, one or more residues in the native relaxin molecule may be substituted with non-naturally encoded amino acids and optionally further modified by covalent attachment of a water soluble polymer, such as PEG. Further description of suitable modified relaxin polypeptides is described in U.S. Pat. No. 8,735,539, to which the skilled reader is directed and the entire contents of which are hereby incorporated by way of reference.

Further, one embodiment of the invention is a fusion polypeptide comprising A-L-B, wherein A comprises a Relaxin A chain polypeptide or a functional variant thereof, B comprises a Relaxin B chain polypeptide or a functional variant thereof and L is a linker polypeptide. In one embodiment the linker polypeptide L of the aforementioned fusion polypeptides A-L-B consists of a polypeptide which is 6-14 amino acid residues in length. Further preferred are polypeptide linkers L which are 7-13 amino acid residues in length. Further preferred are polypeptide linkers L which are 8-12 amino acid residues in length. Even more preferred are polypeptide linkers L which are 7-11 or 9-1 1 amino acid residues in length. Further description of suitable modified relaxin polypeptides are described in WO2013004607 and WO2015/067113, to which the skilled reader is directed and the entire contents of which are hereby incorporated by way of reference.

The skilled person will appreciate that homologues or variants of the proteins or polypeptides of the invention will also find use in the context of the present invention, i.e. able to bind to the relaxin receptor. Thus, for instance proteins or polypeptides which include one or more additions, deletions, substitutions or the like are encompassed by the present invention. In addition, it may be possible to replace one amino acid with another of similar "type". For instance replacing one hydrophobic amino acid with another hydrophobic amino acid.

One can use a program such as the CLUSTAL™ program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment.

"% identity" is a measure of the relationship between two nucleic acid or polypeptide sequences, as determined by comparing their sequences. In general, the two sequences to be compared are aligned to give a maximum correlation between the sequences. The alignment of the two sequences is examined and the number of positions giving an exact amino acid or nucleotide correspondence is determined, and divided by the total length of the alignment, and the result is multiplied by 100 to give a % identity. The % identity may be determined over the whole length of the sequence to be compared, which is particularly suitable for sequences of the same or similar lengths or for sequences which are highly homologous, or over shorter defined lengths which is more suitable for sequences of unequal lengths and with a lower homology.

Methods for comparing the identity of two or more sequences are known in the art, For example, programs available in the Wisconsin Sequence Analysis Package version 9.1 (Devereux J et al., *Nucl Acid Res* 12 387-395 (1984), available from Genetics Computer Group, Madison, Wis., USA), such as BESTFIT and GAP may be used.

BESTFIT uses the "local homology" algorithm of Smith and Waterman (Advances in Applied Mathematics, 2:482-489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (J. Mol. Biol. 48:443-354, 1970). GAP is more suited to comparing sequences which are approximately the same length and an alignment is expected over the entire length. Preferably, the parameters "Gap Weight" and "Length Weight" used in each program are 50 and 3 for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul et al, *J Mol. Biol.*, 215:403-410, (1990) and Altschul et al, *Nuc Acids Res.*, 25:289-3402 (1997), available from the National Center for Biotechnology Information (NCB), Bethesda, Md., USA and accessible through the home page of the NCBI at www.ncbi.nlm.nih.gov) and FASTA (Pearson W. R. and Lipman D. J., *Proc. Nat. Acac. Sol., USA,* 85:2444-2448 (1988), available as part of the Wisconsin Sequence Analysis Package). Preferably, the BLOSUM62 amino acid substitution matrix (Henikoff S. and Henikoff J. G., *Proc. Nat. Acad. Sci., USA,* 89:10915-10919, (1992)) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

In the case of homologues and variants, the degree of identity with a protein or polypeptide as described herein is less important than that the homologue or variant should retain the functionality of the original protein or polypeptide. However, suitably, homologues or variants having at least 60% similarity (as discussed above) or identity with the proteins or polypeptides described herein are provided. Preferably, homologues or variants having at least 70% similarity or identity, more preferably at least 80% similarity or identity are provided. Most preferably, homologues or variants having at least 90% or even 95%, 98% or 99% similarity or identity are provided.

For fragments of the proteins or polypeptides described herein, or of homologues or variants thereof, the situation is slightly different. It is well known that is possible to screen a protein or polypeptide to identify the binding regions, i.e. those regions which are responsible for the protein or polypeptide's functionality. Methods for carrying out such screening are well known in the art. Thus, the fragments of the present invention should include one or more such binding regions or be sufficiently similar to such regions to retain their functional properties. Thus, for fragments according to the present invention the degree of entity is perhaps irrelevant, since they may be 100% identical to a particular part of a protein or polypeptide, homologue or variant as described herein. The key issue, once again, is that the fragment retains the functional properties. In the present application, fragments are any contiguous 10 amino acid sequence, or greater, such as 20, 30, 40, or 50 amino acid sequence.

Naturally occurring biologically active relaxin may be derived from human, murine (ie rat or mouse), porcine or other mammalian sources. The term "Relaxin" encompasses human H1 preprorelaxin, prorelaxin and relaxin; H2 preprorelaxin, prorelaxin and relaxin; recombinant human relaxin (rhRLX); and H3 preprorelaxin, prorelaxin and relaxin. H3 relaxin has been described in the art (see for example Sudo et al (2003) J. Biol. Chem 7; 278(10):7855-62). The Relaxin proteins of the present invention can be obtained from any known source, including isolation from human or animal plasma, as well as human or animal organs. For instance, a form of porcine pituitary Relaxin could be used. However, it is usually more convenient to produce the proteins recombinantly. Such methods for producing the proteins are well known to those skilled in the art.

Several sources for these methods are identified in U.S. Pat. No. 5,166,191 including the following references: Barany et al., The Peptides 2, 1 (1980); Treager et al., Biology of Relaxin and its Role in the Human, pp. 42-55; EP251,615; EP107,782; EP 107,045; and WO 90/13659.

All variations of relaxin described above fall within the scope of the present invention provided that the primary physiologic and biologic functional activity of relaxin is maintained.

Specific examples of relaxin which may be used in accordance with the present invention include Vitalaxin which is porcine relaxin combined with trypsin inhibitor, bovine colostrum, biotin and L-leucine and Serelaxin which is a recombinant form of human relaxin-2.

The amino acid sequences of human relaxin are described in the art. For example, human relaxin amino acid sequences are found under the following Gen Bank Accession Nos.: Q3WXF3, human H3 prorelaxin; P04808, human H1 prorelaxin; NP-604390 and NP-005050, human H2 prorelaxin; AAH05956, human relaxin 1 preproprotein; NP-008842, human H1 preprorelaxin; etc.

As well as providing polypeptides which comprise the Relaxin molecules as defined herein, the present invention also provides nucleic acids and nucleic acid vectors comprising nucleic acids which are capable of expressing the Relaxin molecules. Such nucleic acids and vectors may be used for gene therapy.

Within the context of the present invention, "gene therapy" refers the use of nucleic acid molecules, vectors or compositions comprising the same in the treatment of a patient in need thereof. The nucleic acid molecules, vectors and compositions comprising the same are used in the treatment of an inflammatory, autoimmune or neurodegenerative condition, other than MS wherein cells are transfected or transduced with said nucleic acid molecules. As a consequence of the transfection, these cells express the encoded protein(s). Expression of the nucleic acids and/or proteins leads to the expression of Relaxin in the cells. Gene therapeutic methods according to the invention may rely on viral or non-viral methods as explained below.

The invention further provides a vector comprising a nucleic acid molecule according to the invention. In one embodiment, the vector is a viral vector. In another embodiment, the viral vector is a lentiviral vector, an adeno-associated virus-2 (AAV-2) vector, an adenoviral vector, a retroviral vector, a polio viral vector, a murine Muloney-based viral vector, an alpha viral vector, a pox viral vector, a herpes viral vector, a vaccinia viral vector, a baculoviral vector, a parvo viral vector, or any combination thereof. In one embodiment, a vector of the invention further comprises a carrier. In another embodiment, the carrier is a lipid. In another embodiment, the carrier is a polypeptide.

In a further aspect, the present invention relates to nucleic acid molecules or nucleic acid constructs, e.g. vectors, encoding a Relaxin or a functional variant of homologue thereof. These nucleic acid molecules are suitable for use in gene therapy. The encoded proteins are capable of treating an inflammatory, autoimmune or neurodegenerative condition, other than MS.

In a further embodiment, a nucleic acid molecule of the invention further comprises one or more nucleotide sequences regulating gene activity, e.g., promoters, which may be natural promoters of the genes used herein or exogenous promoter operably linked to the genes used herein. The promoter sequences may be derived from other genes as well as artificial promoters such as chimeric promoters that combine nucleic acid sequences derived from various sources, i.e. different genes that may originate from different species. Further gene activity regulating sequences are transcription factor binding elements (enhancers), wherein the transcription factor binding elements (enhancers) are operably linked to the nucleic acids used herein. Promoters and enhancers that may be used in nucleic acid constructs are known to the person skilled in the art and may be selected, e.g. depending on the type of cell to be transfected, etc., with substantial information available for example via www.genetherapynet.com or common textbooks, e.g. Le Doux, J. (Ed.), Gene Therapy Protocols Vol. 1; Production and In vivo applications of Gene Transfer Vectors, Meth. Mol. Biol., Humana Press (2008).

In certain embodiments, a nucleic acid encompassed by the invention is delivered to a cell. Methods for delivery of a nucleic acid to a cell in vitro or in vivo are known to those skilled in the art. For example, such methods may include the use of peptides, lipids or organic molecules as nucleic acid carriers to facilitate or enhance the cellular uptake of a nucleic acid. Non-limiting examples of such nucleic acid delivery methods and nucleic carriers are described in U.S. Pat. Nos. 6,344,436, 6,514,947, 6,670,177, 6,743,779, 6,806,084, and 6,903,077. The targeting of vehicles for the delivery of the nucleic acid molecules of the invention may be facilitated by the use of target cell specific molecules, e.g. receptor recognizing structures on the target cells. These receptors may be immunoglobulin derived.

Compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will of course depend on the route of administration and the age, weight and condition of the patient and will be at the doctor's discretion.

The compositions of the invention may be adapted for administration by any appropriate route, for example by the oral (including buccal or sublingual), nasal, topical (including buccal, sublingual or transdermal) or parenteral (including subcutaneous, intramuscular, intravenous or intradermal) route. Such formulations may be prepared by any method known in the art of pharmacy, for example by bringing into association the active ingredient with the carrier(s) or excipient(s).

The term "carrier" is used herein to refer to a pharmaceutically acceptable vehicle for a pharmacologically active agent. The carrier facilitates delivery of the active agent to the target site without terminating the function of the agent. Non-limiting examples of suitable forms of the carrier include solutions, creams, gels, gel emulsions, jellies, pastes, lotions, salves, sprays, ointments, powders, solid admixtures, aerosols, emulsions (e.g., water in oil or oil in water), gel aqueous solutions, aqueous solutions, suspensions, liniments, tinctures, and patches suitable for topical administration.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

The formulations of the present invention may comprise at least one further active ingredient, such as estrogen, or other hormones, cytokines and the like. Thus, in a further aspect the present invention provides a formulation comprising relaxin (RLX), a homologue or variant thereof as defined herein, in combination with at least one further active ingredient, such as estrogen for use in a method of treating a condition as defined herein above.

The present invention will now be further described with reference to the following figures which show.

EXAMPLES SECTION

Materials and Methods

Animals and Treatment

Female C57BL/6 mice were obtained and housed at Biomedical Research Models (Worcester, Mass.)

At 7-8 weeks of age, mice were immunized with MOG33-35/CFA emulsion (Hooke Laboratories #EK-2110 provided pre-formulated). Mice received pertussis toxin (Hooke Laboratory, Cat #EK-2110 provided lyophilized) reconstituted in phosphate buffered saline (PBS) at the time of immunization (day 0; 75 ng) and on day 2 (200 ng). Animals were scored daily for disease severity: 0=normal, 1=tail paralysis, 2=tail paralysis and strong hind limb weakness, 3=complete hind limb paralysis, 4=hind limb and forelimb paralysis, 5=found dead.

At the onset of EAE (the first day with a score of 1 or greater), subcutaneous alzet pumps (DURECT Corporation, Cupertino, Calif.) were inserted and the animals were randomly assigned to receive either porcine relaxin (SKY BioHealth, Inc., Eden Prairie, Minn., 66.0 µg/day) or placebo treatment (1 µ/Hr PBS), either recombinant porcine relaxin (pRLN, n=8) or placebo (PBS, n=8) at a rate of 0.110/hr. Relaxin (SKY BioHealth, Inc., Eden Prairie, Minn/) was administered at a concentration of 0.25 mg/ml for the remainder of the study. This delivered a standard dose of 0.66 µg/day of pRLN, which is equivalent to the identified effective dose of 30 µg/KG body weight/day (Hasse et al, 2014). Statistical analysis was done using the t-test and P values <0.05 were considered to be statistically significant.

Spinal Cord

Spinal cords and brains were collected for RT-PCR and histopathology. Total RNA was isolated from spinal cord and brain tissue using the RNeasy mini-kit protocol (Qiagen; Valencia, Calif.) and converted to cDNA using oligo(dT), random hexamers, and Superscript RT II (Invitrogen; Grand Island, N.Y.). RT-PCR for CCR2, CCR5, CCR7, IL-6, IL-10, IL-17 and TNF-α was run on a Prism 7000 sequence detection system (Applied Biosystems; Foster City, Calif.) using Taqman PCR master mix (Qiagen) and primers from Applied Biosystems. Levels of expression were normalized to β-actin. Alternatively RT-PCR for the chemokine receptors (CCR); CCR2, CCR5, CCR7, the interleukins (IL-6 and IL-17) were analyzed using quantitect primers (table 2) and SYBR green based RT-PCR kits (Qiagen, Valencia, Calif.). For histology, spinal cords sections were stained using luxol fast blue-periodic acid shiff for semi-quantitative analysis of infiltration and demyelination.

For alternative histology, spinal cords were formalin fixed and paraffin embedded (FFPE) as described by Canene-Adams [Canene-Adams, 2013]. Briefly, Spinal cords were rinsed in PBS to remove blood and fixed in 10% formalin for 48 hours at room temperature. Tissues were then transferred to 70% ethanol (ETOH) for 1 hour, 95% ETOH (95% ETOH/5% methanol) for 1 hour, then incubated in four absolute ETOH baths first for 1 hour, then 2 for 1½ hours, followed by a fourth for 2 hours. Tissues were then cleared with two xylene baths for 1 hour each. Tissues were then incubated in two paraffin baths at 58° C. for 1 hour each. Tissues were then removed and placed in cassettes.

The FFPE tissues were sectioned into 5 μM slices on a microtome. Slices were transferred to glass slides and warmed to 65° C. for 20 minutes to bond the tissue to the glass.

Sections were stained with Kiernan's eriochrome cyanin for myelin [Kiernan J A, 1999], cluster of differentiation 68 (CD68) for macrophages [Holness and Simmons, 1993], neurofilaments [Alberts, B. 2002] and glial fibrillary acidic protein (GFAP) [Jacque C M, et al, 1978].

Kiernan's stain for myelin was done as described. First tissues were placed in a solution containing eriochrome cyanine R, ferric chloride and sulphuric acid in water for 20 minutes. Rinsed briefly under tap water and differentiated with aqueous ferric chloride (5.6%). Tissues were then dried with ETOH.

Staining with Hematoxylin and eosin (H&E) stain was also carried out according to standard protocols.

Standard immunohistochemistry [Ramos-vara and Miller, 2014] was used to identify the presence of CD68, neurofilaments and GFAP in the FFPE tissues. Essentially the appropriate antibody directed against the antigen of choice was incubated with the tissue and allowed to bind. The tissue was then washed and incubated with the secondary antibody which was conjugated to the dye. The tissues were then washed and the conjugated dye developed for visualization.

Results

Disease Severity

Figure 1:
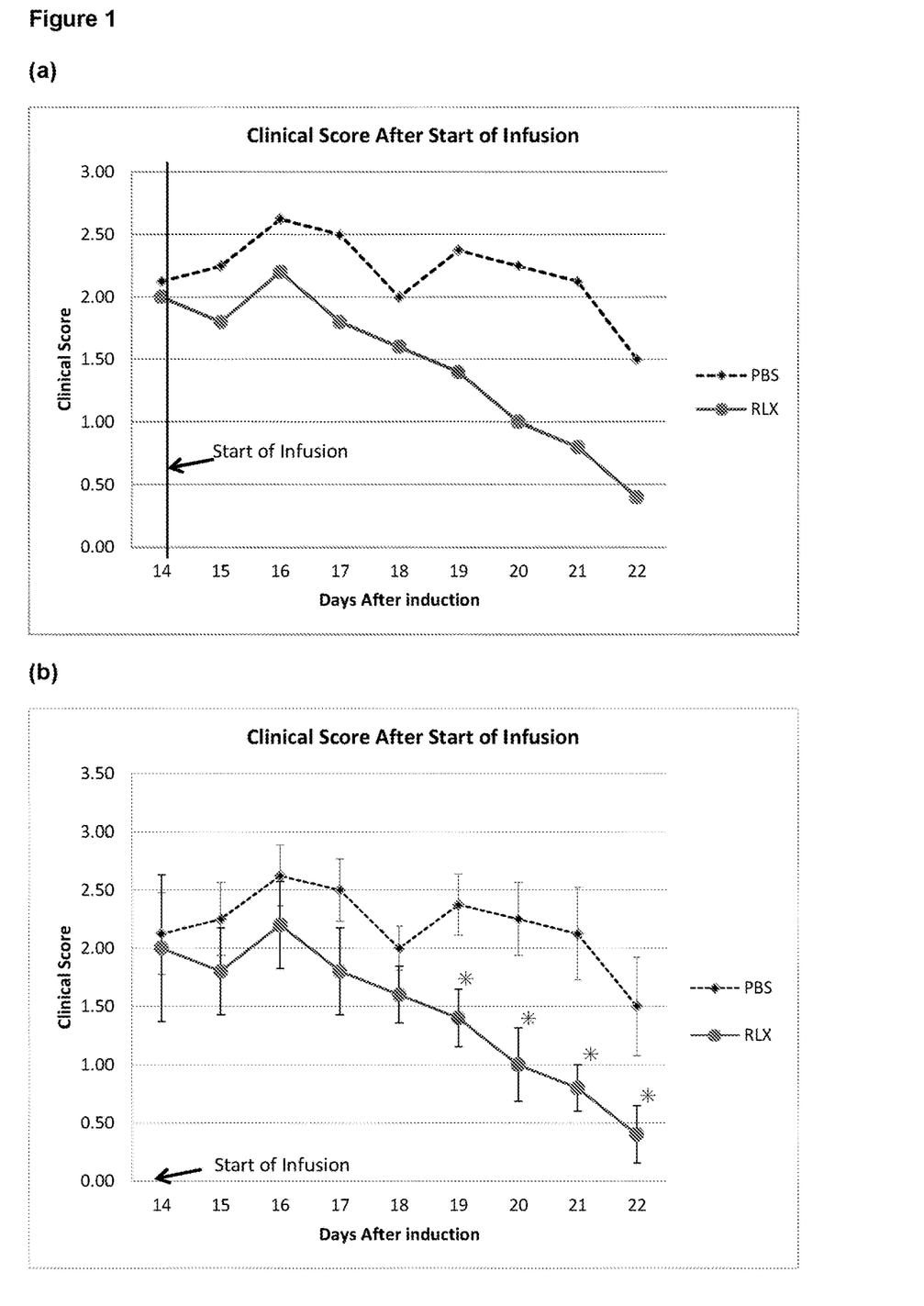
FIG. 1*a* shows the improvement in clinical score in EAE model animals receiving RLX, as compared to PBS control. Improvement in clinical scores; 0=normal, 1=tail paralysis, 2=tail paralysis and strong hind limb weakness, 3=complete hind limb paralysis, 4=hind limb and forelimb paralysis, 5=found dead.
FIG. 1*b* shows similar results to 1a—Animals receiving RLN treatment (n=8) showed greater improvement in clinical scores (2.0->0.5) compared to the placebo treated group (n=8, 2.0-1.5). Using a scale of 0-5 (0=normal, 1=tail paralysis, 2=tail paralysis and strong hind limb weakness, 3=complete hind limb paralysis, 4=hind limb and forelimb paralysis, 5=found dead). (*=p<0.05).

Clinical onset of EAE was detected on day 14 of the study. The alzet pumps were inserted in the mice and continuous infusion of either RLX or PBS was started. Animals receiving RLX treatment showed a marked improvement in clinical score within 3 days of commencing treatment (FIG. 1a). In further studies at the end of treatment the group receiving RLN treatment had a score of >0.5 while the placebo group had a score 1.5. The difference in scores between the RLN and placebo treated group were significant on days 19, 20, & 21 ($p=<0.05$), see FIG. 1b).

Real-Time PCR

Levels of mRNA for cytokines and chemokine receptors were analysed in the spinal cord samples.

Figure 4:
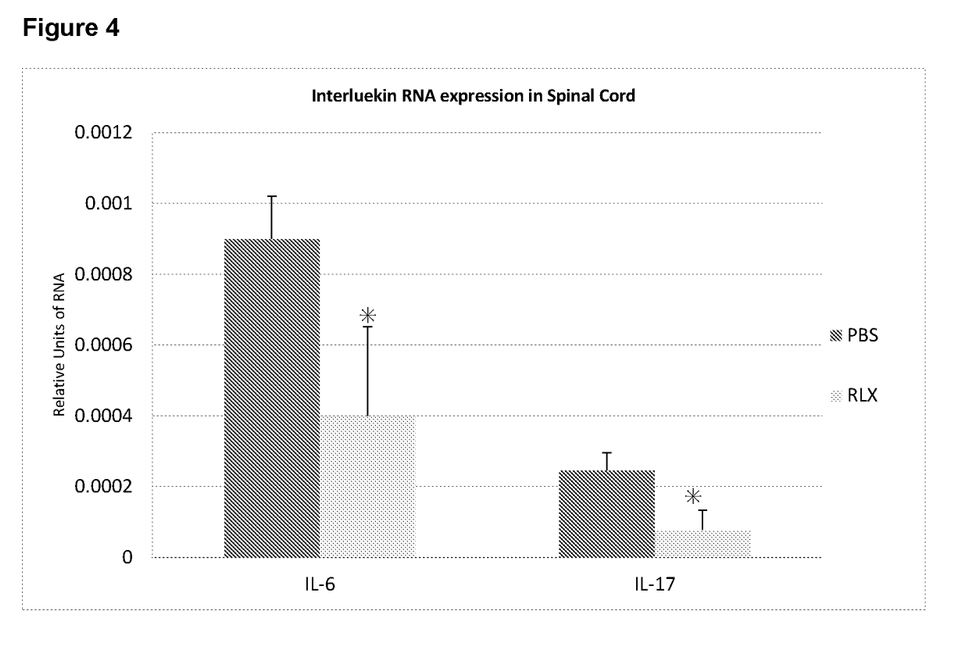
FIG. 4 shows spinal cord expression of cytokines in relative units normalised to β-actin spinal cord tissue. The cytokines IL-6 and IL-17 were significantly decreased in the relaxin treated group (n=8) when compared to the placebo group (n=8). (*=p<0.05)

Further studies show that in comparison to the placebo group (n=8) RNA in the spinal cords of the relaxin treated group (n=8) showed a significant decreases in the chemokine receptors CCR2 (0.13 vs 0.044, $p<0.05$) and CCR7 (0.003 vs 0.014, $p<0.05$). There was also an observed decrease in CCR5 (0.0035 vs 0.0046) although this was not significant (see FIG. 2b). There was also a reduction in the cytokines IL-6 (0.0004 vs 0.0009, $p<0.05$) and IL-17 (0.000078 vs 0.00026, $p<0.05$, see FIG. 4).

Figure 2:
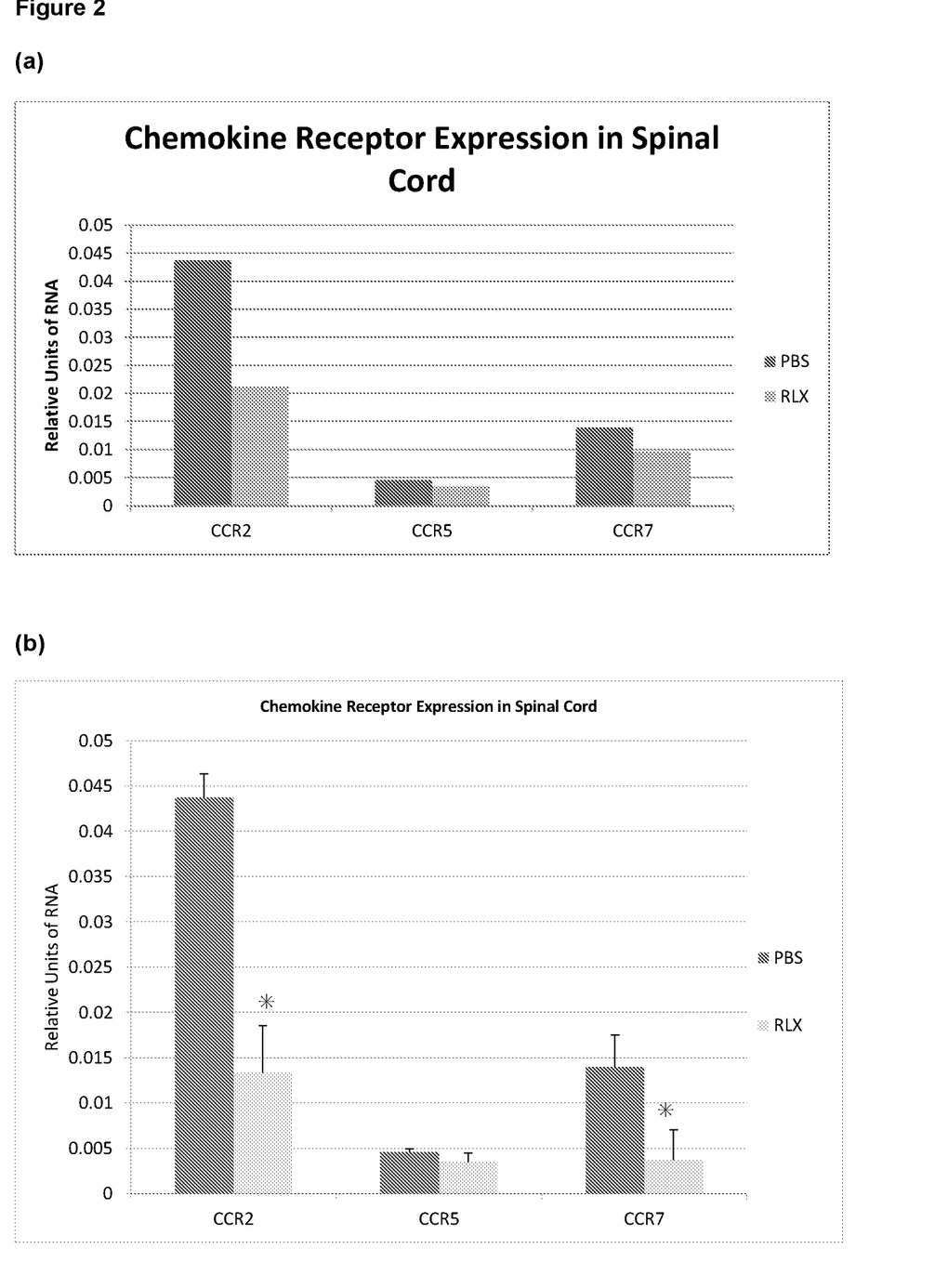
FIG. 2*a* shows the reductions in chemokine receptors in relative units normalised to β-actin following RLX treatment, as compared to PBS control. The pro-inflammatory chemokine receptors CCR2, CCR5 and CCR7 were decreased in relaxin treated mice
FIG. 2*b* shows similar results to 2a—spinal cord expression of chemokine receptors in relative units normalized to β-actin. The pro-inflammatory chemokine receptors CCR2, CCR5 and CCR7 were decreased in relaxin treated mice (n=8) when compared to the placebo group (n=8). (*=p<0.05)
Figure 3:
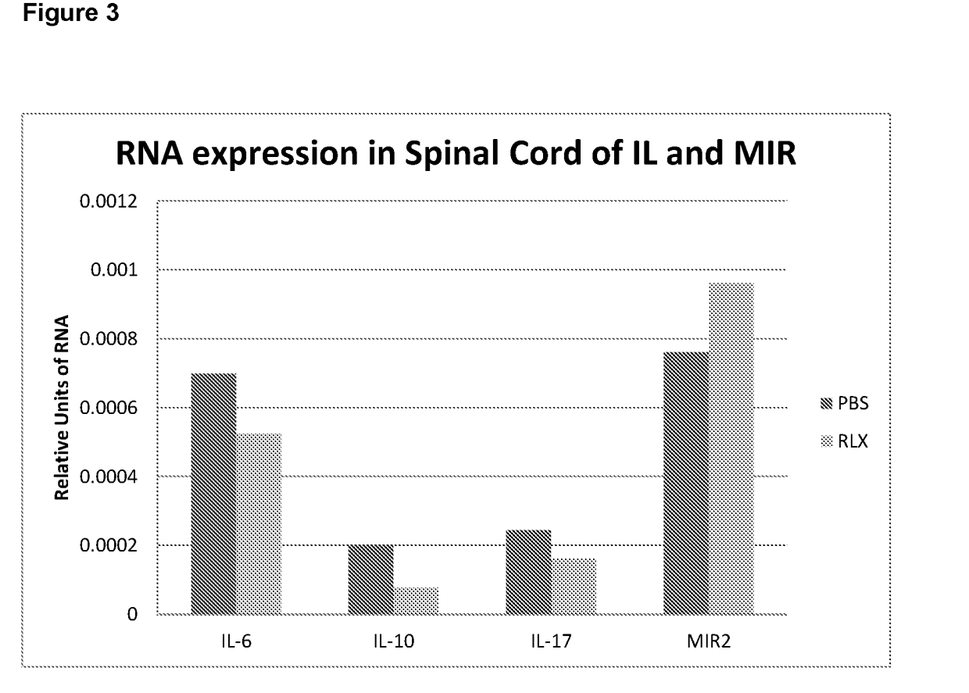
FIG. 3 shows spinal cord expression of cytokines in relative units normalised to β-actin spinal cord tissue. The cytokines IL-6, IL-10 and IL-17 were decreased and MIR2 was increased in relaxin treated mice.

RNA expression in the spinal cords of relaxin treated mice showed significant reductions in the chemokine receptors CCR2, CCR5 and CCR7 (see FIG. 2a). The cytokines IL-6, IL-10 and IL-17 were also decreased in the RLX treated mice (see FIG. 3).

Histology

Relaxin treatment reduced lesion load and size which indicates a decrease in cellular infiltration into the spinal cord compared to control animals (data not shown).

Kiernan's Eriochrome Cyanin for Myelin and H&E Staining

Figure 5:
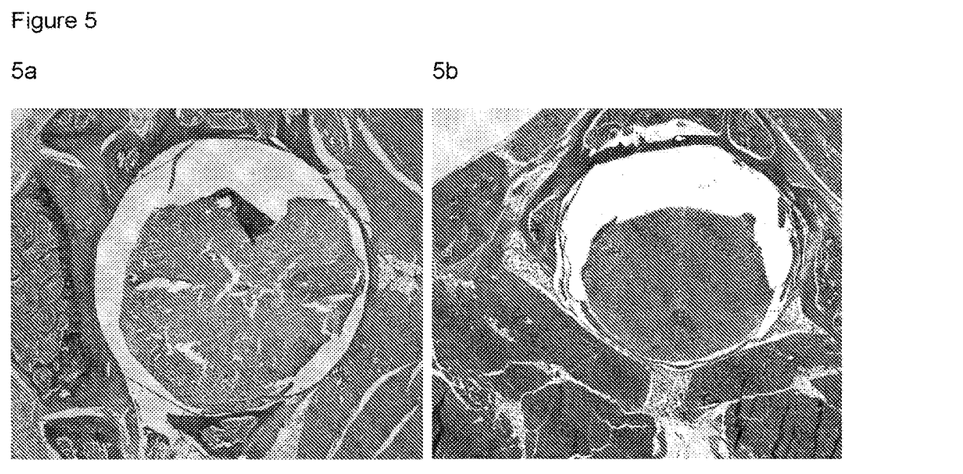
FIG. 5 shows cross sections of spinal cord where myelin is stained blue. The decrease in blue colour indicates demyelination in untreated mice (1a). Whereas, mice treated with RLN (2b) have normal appearing myelin which stains an intense blue. Images are enlarged 40×.

The spinal cords of mice with EAE which were untreated showed inflammation, Wallerian degeneration and a loss of myelin. While mice treated with RLN had normal appearing myelin (see FIGS. 5 and 6).

CD68

Figure 6:
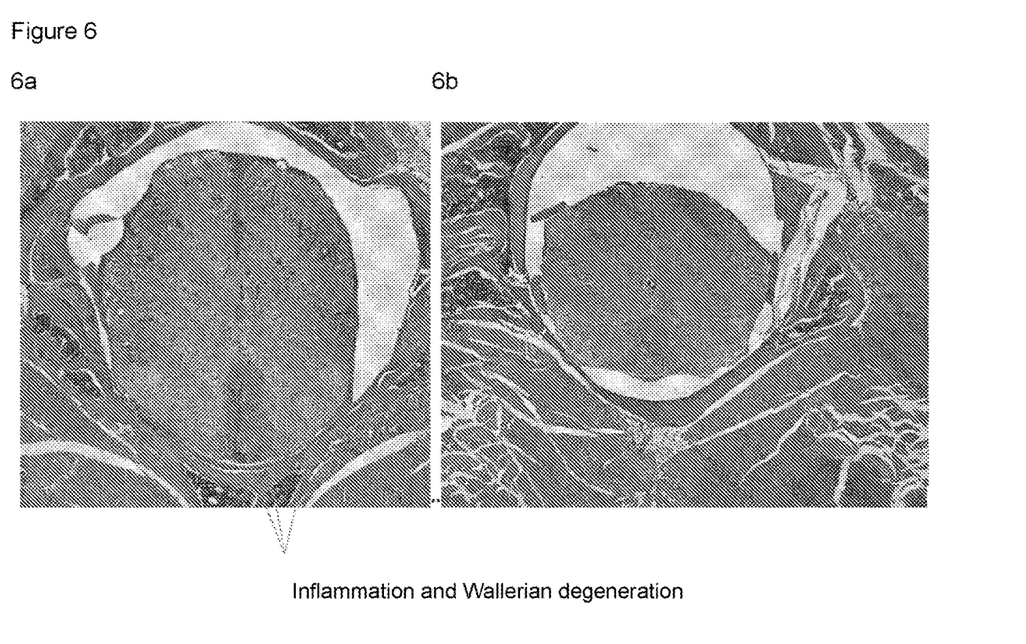
FIG. 6 shows a decrease in inflammation and Wallerian degeneration of the spinal cord using H&E staining, following treatment with Relaxin (b) as compared to untreated spinal cord (a).

Tissue samples stained for the presence of CD68 showed greater infiltration of macrophages in the untreated samples than in those treated with RLN (see FIG. 6).

Neurofilaments

Figure 7:
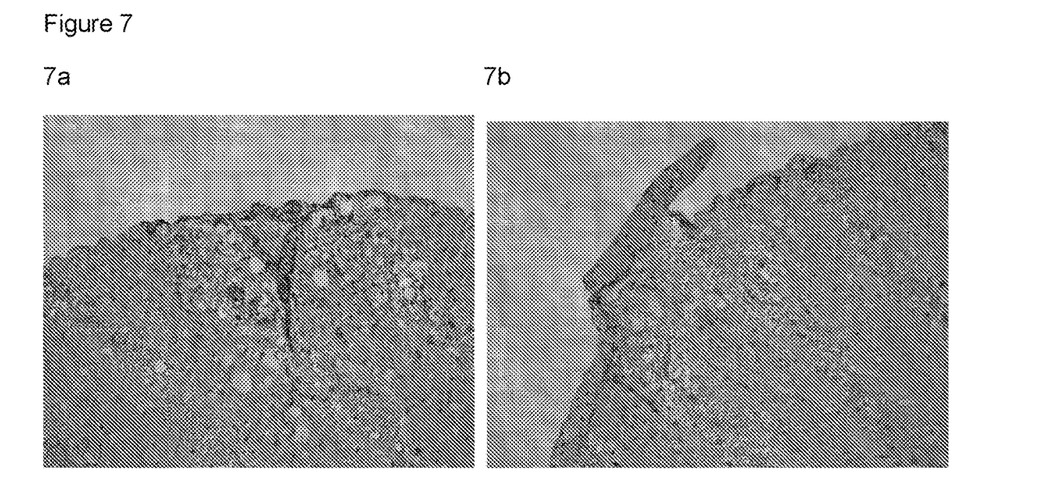
FIG. 7 shows decreased macrophage infiltration of the spinal cord of RLN treated mice (7b) when compared to untreated mice (7a). Tissue samples were embedded in paraffin and stained for CD68. Images are magnified 200×.

The spinal cords from untreated mice shoed a relatively greater loss of neurofilaments compared to mice receiving RLN therapy (see FIG. 7).

GFAP

Figure 8:
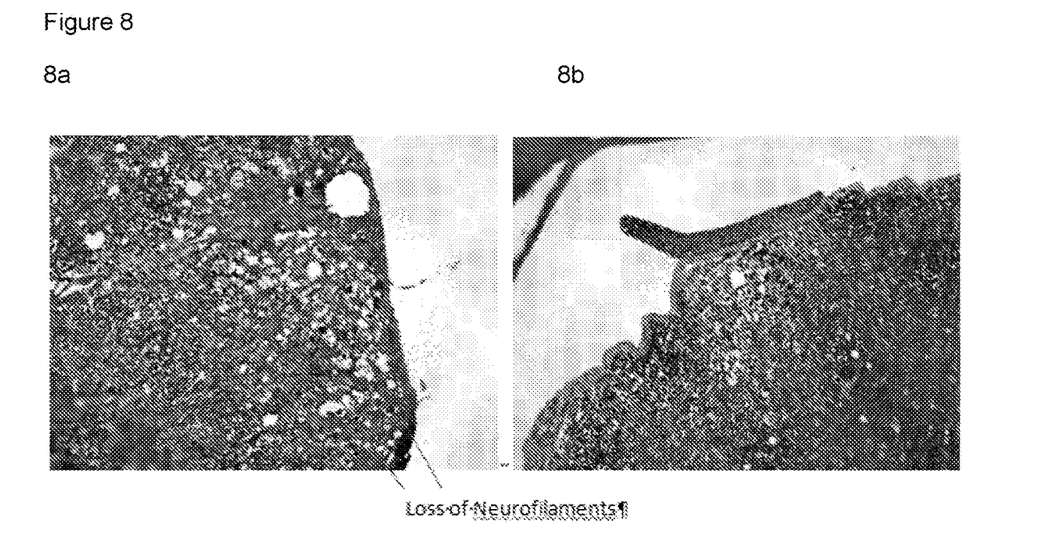
FIG. 8 indicates a greater loss of neurofilament in the spinal cords of untreated mice (8a) compared to mice treated with RLN (8b). Indicating a loss of neurons in the untreated mice as compared to those treated with RLN. Images are magnified 200×.
Figure 9:
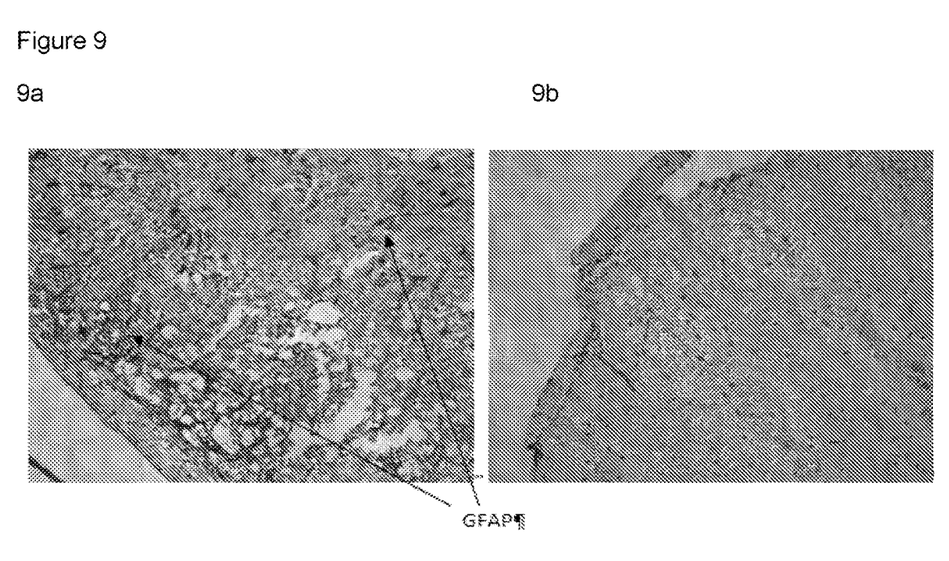
FIG. 9 shows spinal cord slices stained for the presence of GFAP. The untreated sample (9a) has large amounts of GFAP present indicating extensive gliosis. In contrast, the RLN treated samples did not stain positively for GFAP. Magnification 200×.

The spinal cords for RLN treated mice were negative for GFAP while the untreated mice stained positive for GFAP, indicating the presence of gliosis (see FIG. 8).

Discussion

Inflammatory autoimmune diseases of the CNS which include MS and EAE may differ in onset and etiology, but the goals of treatment are the same; control inflammation, regulate autoimmunity and enhance neural protection. Despite the development of agents capable of modulating inflammation and autoimmunity, treatment remains problematic. Low efficacy and severe side effects being the most limiting factors in the use of these agents (Costello 2008).

The discovery that estrogen treatment could reduce the relapse rate and symptoms in MS (Sicotte 2002) provided a novel approach to treatment based on a naturally occurring peptide. But estrogen is not without unwanted side effects, especially with prolonged use (Barrett-Connor 2001). The challenge of using sex hormone-based therapy for these diseases is to maximize the effects of this treatment on the immune system and minimize the effects on the reproductive system. By studying the actions of molecules produced downstream from estrogen may identify one which has many of the immune-modulating effects with minimum or no effect of the reproductive system. In this study we investigated the ability of one such molecule, RLX in the treatment of EAE. The results of which showed that like estrogen, it down regulated the secretion of pro-inflammatory cytokines and chemokine receptors, reduced cellular infiltration and demyelination in EAE. And increased the expression of the MIR2, which can downregulate a wide range of cell surface proteins (Anania 2011) including the major histocompatability complex 1 (MHC-1, Thakur 2011).

In addition, treatment with RLN down regulated the secretion of pro-inflammatory chemokine receptors CCR2 and CCR5. These results are significant since CCR2 has been identified as a key driver of encephalitogenic Th17 cell recruitment into the CNS in MS and EAE. Molecules capable of modulating CCR2 have been identified as possible novel therapies in MS and EAE (Kara et al, 2015). Similarly, CCR5+ Th-1 cells are increased in the CSF and brain lesions of active demyelinating MS patients. Glatiramer acetate which is widely used for treatment of MS, acts via decreasing the expression of CCR5 and related Th-1 cells (Cheng and Chen, 2014). Th-1 and Th-17 cells are also modulated by CCR7, the presence of which is required for the development of EAE (Kuwabara, 2009).

Modulation of the cytokines IL-6 and IL-17 by RLN also has implication for novel therapeutic strategies in MS and EAE. Therapies that reduce IL-6 levels in EAE reduce symptoms and disease progression (Erta, 2016). And the pro-inflammatory cytokine IL-17 is a crucial effector cytokine. Therapies designed to block or reduce levels of IL-17 has been shown to be effective treatments in EAE (Hofstetter et al, 2005). Novel therapies targeted at blacking or reducing IL-6 and IL-17 are currently undergoing clinical trials for the treatment of MS.

The results of histology and immunohistochemistry showed a reduction of infiltrating macrophages in the RLN treated group. There was evidence of neuroprotective effects from RLN treatment as it reduced demyelination, preserved neurofilaments, protected neurons and stopped or reversed gliosis.

RLX treatment can ameliorate the symptoms of EAE, reduce lesion load and modulate the expression of cytokines and chemokine receptors. It is a naturally occurring peptide capable of modulating the ER's, GCR and PPARγ; pathways known to modulate the symptoms of MS. And in limited clinical trials there have been no severe side effects reported with its use (Smith 2006;). These results taken together with ability of RLX to modulate some of the pathways currently targeted in the treatment of MS, support further investigation of RLX as a novel therapeutic pathway in treating MS and other inflammatory, neurodegenerative and inflammatory auto-immune diseases and conditions.

REFERENCES

Barrett-Connor E and Stuenkel C A. Hormone replacement therapy (HRT)—risks and benefits Int. J. Epidemiol. 2001;30(3):423-426. doi:10.1093/ije/30.3.423.

Costello K, Kennedy P, Scanzillo J. Recognizing Nonadherence in Patients With Multiple Sclerosis and Maintaining Treatment Adherence in the Long Term. Medscape J Med. 2008;10(9):225.

Sicotte N L, Liva S M, Klutch R, Pfeiffer P, Bouvier S, Odesa S, Wu T C, Voskuhl R R. Treatment of multiple sclerosis with the pregnancy hormone estriol. Ann Neurol. 2002;52(4):421-8. DOI: 10.1002/ana.10301.

Smith M C, Danielson L A, Conrad K P, Davison J M. Influence of Recombinant Human Relaxin on Renal Hemodynamics in Healthy Volunteers. JASN. 2006;17:3192-3197. doi:10.1681/ASN.2005090950.

Constantinescu C S, Farooqi N, O'Brien K, Gran B. Experimental autoimmune encephalomyelitis (EAE) as a model for multiple sclerosis (MS). British Journal of Pharmacology. 2011;164(4):1079-1106.

He F, Balling R. The role of regulatory T cells in neurodegenerative diseases. Wiley Interdiscip Rev Syst Biol Med. 2013 March-April; 5(2):153-80.

Olive Leavy. T cells: Two faces of EAE. Nature Reviews Immunology 8, 576 (2008).

Anderton S M. Treg and T-effector cells in autoimmune CNS inflammation: a delicate balance, easily disturbed. Eur J Immunol. 2010 December; 40(12):3321-4.

M. Schwartz, A. London, R. Shechter. Boosting T-cell immunity as a therapeutic approach for neurodegenerative conditions: The role of innate immunity. Neuroscience, *Volume* 158, Issue 3, Pages 1133-1142.

Weiner H L. Multiple sclerosis is an inflammatory T-cell-mediated autoimmune disease. Arch Neurol. 2004 October; 61(10):1613-5.

Shao H, Huang Z, Sun S L, Kaplan H J, Sun D. Myelin/oligodendrocyte. glycoprotein-specific T-cells induce severe optic neuritis in the C57BL/6 mouse. Invest Ophthalmol Vis Sci. 2004 November; 45(11):4060-5.

Garg R K. Acute disseminated encephalomyelitis. Postgrad Med J 2003;79:927 11-17

Bellone, Matteo(September 2010) Autoimmune Disease: Pathogenesis. In: eLS. John Wiley & Sons Ltd, Chichester. http://www.els.net.

Cai Y, Fleming C, Yan J. New insights of T cells in the pathogenesis of psoriasis. Cellular & Molecular Immunology (2012) 9.

The invention claimed is:

1. A method of treating traumatic spinal cord injury comprising administering an effective amount of relaxin selected from human relaxin 1 and relaxin 2, a homologue selected from prorelaxin and preprorelaxin or variant thereof to a subject in need thereof, wherein the relaxin, the homologue or the variant thereof is a polypeptide, wherein the variant thereof has at least 95% similarity or identity to the relaxin or the homologue, and wherein administration of the relaxin, the homologue or the variant thereof reduces the levels of IL-6 and IL-17 in the spinal cord and brain, reduces demyelination, preserves neurofilaments, protects neurons, and stops or reverses gliosis.

2. The method according to claim 1, wherein the method further comprises the administration of estrogen.

3. The method according to claim 1, wherein the variant thereof has at least 98% similarity or identity to the relaxin or the homologue.

* * * * *